United States Patent
Impellizzeri (10) Patent No.: US 6,802,421 B1
(45) Date of Patent: Oct. 12, 2004

(54) DEVICE FOR HANDLING AND IDENTIFYING SMALL IMPLANTS

(75) Inventor: Frederic Impellizzeri, Salon de Provence (FR)

(73) Assignee: Biotech International (SARL), Salon de Provence (FR)

( * ) Notice: Subject to any disclaimer, the term of this patent is extended or adjusted under 35 U.S.C. 154(b) by 0 days.

(21) Appl. No.: 10/169,019
(22) PCT Filed: Dec. 30, 1999
(86) PCT No.: PCT/FR99/03323
§ 371 (c)(1), (2), (4) Date: Sep. 16, 2002
(87) PCT Pub. No.: WO01/49198
PCT Pub. Date: Jul. 12, 2001

(51) Int. Cl.$^7$ ................................................ A61L 15/00
(52) U.S. Cl. ................................................ 206/438
(58) Field of Search ................................ 206/438, 63.5

(56) References Cited

U.S. PATENT DOCUMENTS

| | | | | |
|---|---|---|---|---|
| 3,967,621 A | * | 7/1976 | Schwarz | 604/192 |
| 4,712,681 A | * | 12/1987 | Branemark et al. | 206/438 |
| 5,148,920 A | * | 9/1992 | Walker | 206/588 |
| 5,582,299 A | * | 12/1996 | Lazzara et al. | 206/63.5 |
| 5,669,501 A | * | 9/1997 | Hissong et al. | 206/438 |
| 6,006,917 A | * | 12/1999 | Loeffler | 206/583 |
| RE36,693 E | * | 5/2000 | Reich | 250/507.1 |
| 2003/0132131 A1 | * | 7/2003 | Rabiner et al. | |

* cited by examiner

Primary Examiner—Jacob K. Ackun
Assistant Examiner—Faye Francis
(74) Attorney, Agent, or Firm—Harrison & Egbert (57) ABSTRACT

A device for handling and identifying small implants used for the coaptation of bone fragments or osteosynthesis. The device is characterized in that it includes a small implant and a matching identifying support, the support including a body, at least partially made of an elastically deformable material. The body includes a retaining housing whose shape corresponds to that of the small implant matching the support and in which the implant is at least partially accommodated. The support also includes a characterization mechanism enabling it to be identified and hereby rendering the implant that matches the support recognizable.

7 Claims, 8 Drawing Sheets

DEVICE FOR HANDLING AND IDENTIFYING SMALL IMPLANTS

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The invention presented here involves an identifying device for the handling and identification of small implants (screws or other items) used in restoration surgery (orthopedic surgery, maxillo-facial surgery, osteosynthesis, etc.).

In an application that is of very much interest, the identifying device according to-the invention makes it possible to identify and follow the route of an implant having a reduced size (for example, on the order of 1 to 2 mm), from its manufacture to its implantation in a patient.

BACKGROUND OF THE INVENTION

As of a recent date, a directive of the Commission of the European Community requires the tracking capability, i.e. the identification and the tracking of any material having a surgical use intended to be put into position in vivo, from its manufacture to its final usage, for example until it is implanted in a patients body. Each product leaving the factory of manufacture must thus be identified namely by a lot number that must be able to be read and noted at any moment. Thus, if an implant turns out to be defective for any reason, the identification number must make it possible or at least make it easier to determine the origin of the defect.

On the one hand, it is largely desirable that the surgeons or their practicing assistants in a surgical unit can, on the one hand, easily grasp the small implants such as screws used for the coaptation of fragments of bone or other items, and, on the other hand, read and report their number in the patients' files. In addition, as soon as an implant is sterilized, the handling must be as indirect as possible (while staying easy) in order to not contaminate the implant.

The surgical material having a reduced size provided for the surgical unit and intended for implantation on a patient must thus be easily identifiable and easy to handle without its sterilization being compromised.

Modern surgery uses, in certain fields (orthopedics, maxillo-facial surgery, steosynthesis, operations on small bones, small fragments or extremities of the skeleton, ) very small-sized material (less than 2 mm) intended for implantation in the body of a patient.

Currently, the surgical material intended for "in vivo" implantation is delivered to hospitals either already sterilized and packaged in sterile boxes which are brought closed into a surgical unit for implantations or not sterilized. It is then divided into racks or trays by means of which it is then sterilized or autoclaved, before being brought into the surgical unit.

In the first case, which is a very expensive solution, it is easy to place in the boxes, before sterilization, labels containing the lot number, in a manner so that when the boxes are opened for the purpose of using the sterilized material, it is easy to collect the labels and place them in the patients' files.

However, this packaging mode of implants requires the use of a sizeable volume of the boxes, which increases the cost of transport and complicates the storage and handling. Another disadvantage of this packaging mode is that one is sometimes led to open several boxes in order to obtain the necessary parts, while voiding the sterilization of the implants that are not used.

In the second case, the characterization of the implants permitting their identification and the traceability required by the European directive is very difficult to realize.

In fact, the identification number attributed to each implant or to each lot of implants comprises most often a sequence of several numbers and/or letters, and the engraving of this number directly on the implants, though it is possible and standard usage for relatively large implants, becomes almost unrealizable on implants having a reduced size, due to a lack of space. Supposing that a micro-engraving is possible in certain cases, the easy reading of this number, for example, by the surgeon or by one his assistants in the course of the operation would stay impossible, whether to the naked eye or using a magnifying glass. Another possibility would be to use the small space available on each implant in order to engrave signs of recognition occupying a very small surface in the form of a code, but there again, the reading of this code by the medical personnel is impossible without specialized equipment for decoding.

The purpose of the invention is, notably, to correct the disadvantages mentioned above.

BRIEF SUMMARY OF THE INVENTION

According to the invention, this purpose is achieved by an identifying device consisting of a small implant and a matched identifying support, where this support consists of a body made, at least in part, of a material having a capacity for elastic deformation, this body consisting of a retentive housing, for example, a constrictive housing, having a form fitted to that of the small-sized implant matched to this support, and in which the implant is housed, at least in part, and the support consists additionally of a designation mechanism allowing its identification and, as a result, the recognition of the implant matched to this identifying support.

It is understood that according to the invention, each implant is clipped in an identifying support which has, for example, on one of its faces and in a manner that can be read easily, the inscription of the information necessary for the identification of the implant that it carries. The coupled assemblies of the identifying support/implant can be delivered unpackaged, then placed in boxes or containers for sterilization by steam at 138° C. in an autoclave oven. The coupled assemblies of the identifying support/implant can be sterilized as many times as necessary without losing the identifying information of the implant. The device according to the invention thus makes it very easy to identify and handle small surgical implants. The identifying device according to the invention also makes it possible to keep the material in place in the container, notably during the transport of the container.

A very significant advantage of the identifying device according to the invention is that it makes it possible to arrange, on the external surface of the support, a sufficiently large area so that a number or other identification mark can be engraved there so that it is easily readable, during the operation, by the surgeons or their assistants, i.e. at the moment of the implantation of the implants. It is understood that this possibility makes it much easier to obtain the traceability required by the regulatory documents.

The identifying device according to the invention also makes it possible in an advantageous manner to handle the implant using sterile instruments, without touching and thus without contaminating it, for example, when putting the implants, which were received unpackaged, into boxes.

According to another characteristic arrangement, the support of the identifying device according to the invention consists of a lateral slit opening into the retentive housing of the support, the edges of this slit being able to be spread apart or moved together, due to the elasticity of the material.

In this way, the implant or other small object can be put easily and almost instantly into the constrictive housing of the support or also taken out easily and rapidly from this housing.

According to another characteristic of the invention, the support of the identifying device consists of a lateral recess arranged in alignment with the constrictive housing and opening into it.

By this arrangement, the implant, such as a screw or other object, can be easily grasped and brought out from its matched support by means of an appropriate instrument such as previously sterilized forceps or tweezers, which contributes to the preservation of the sterile condition of the implant.

BRIEF DESCRIPTION OF THE SEVERAL VIEWS OF THE DRAWINGS

The above objectives, characteristics and advantages and still others, can be ascertained best from the description that follows and the attached drawings.

DETAILED DESCRIPTION OF THE INVENTION

Reference is made to the drawings in order to describe two embodiment examples that are of interest, but in no way restrictive, of the identifying device according to the invention.

This device consists of a small implant 7 and a matched identifying support 1. The small implant 7 can be made of an osteosynthesis screw used in orthopedic surgery, in maxillo-facial surgery, or other objects.

The identifying support consists of a body 1 made of a material equipped with a capacity for elastic deformation and capable of supporting high temperatures of sterilization in autoclaves, for example, an elastomer material. It can be made as a whole or at least in part of such a material. This may involve a thermoplastic elastomer having a polyethylene and butylene base (central group) and polystyrene (endings), for example, of the type known under the designation "KRATON" (registered trademark).

The body 1 has an elongated form and it consists of a retentive housing 2 whose axis is oriented longitudinally according to an advantageous arrangement of the invention, but which could have other orientations, according to its applications.

In a preferred manner, the retentive housing 2 extends over a part only of the length of the body 1. In this part, the body 1 is provided with a longitudinal slit 3 that opens to the outside, i.e. a slit oriented parallel to the axis of the retentive housing 2 in which the slit opens. It is understood that because of the elasticity of the material in which the body 1 is made, the opposed edges 4a, 4b of the slit 3 can be spread apart from each other, by the application of a spreading force, in order to allow the positioning of a small implant 7 in this housing, or moved together, by the action of elasticity, in a manner so as to keep the implant in place in the housing 2.

In an advantageous manner, the retentive housing 2 has a form complementary to that of the implant to which it is matched. This housing can have a conformation making it possible to hold the implant with a little play or without play. Alternatively or complementarily, the retentive housing 2 can be constrictive, i.e. fitted to exert a tightening action around the implant, by the action of the elasticity of the material. In this case, at rest, the housing has a diameter very slightly less than that of the implant.

Figure 1:
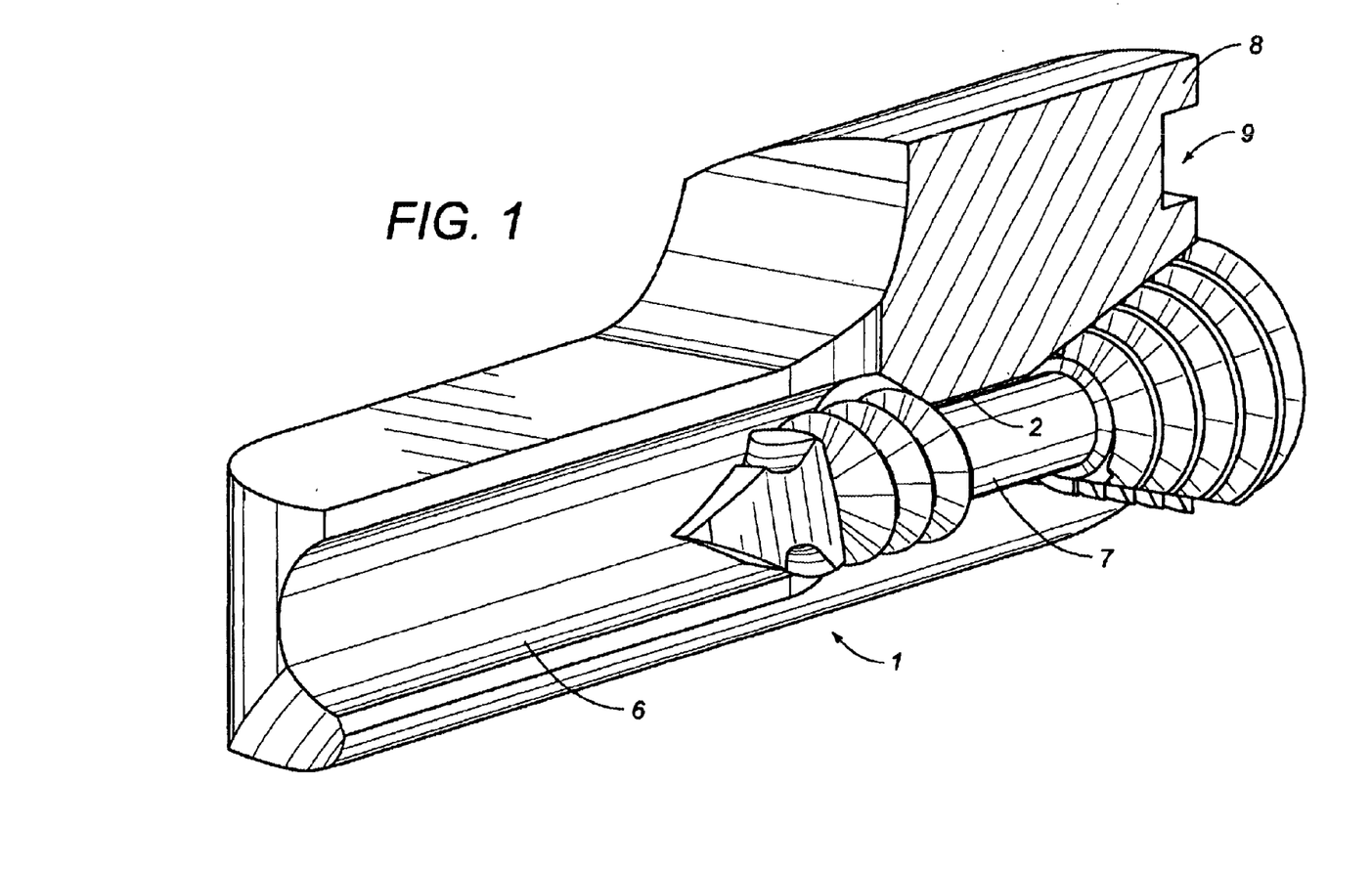
FIG. 1 is a perspective view with a partial extraction of a first embodiment example of the identifying device for small implants according to the invention.
Figure 2:
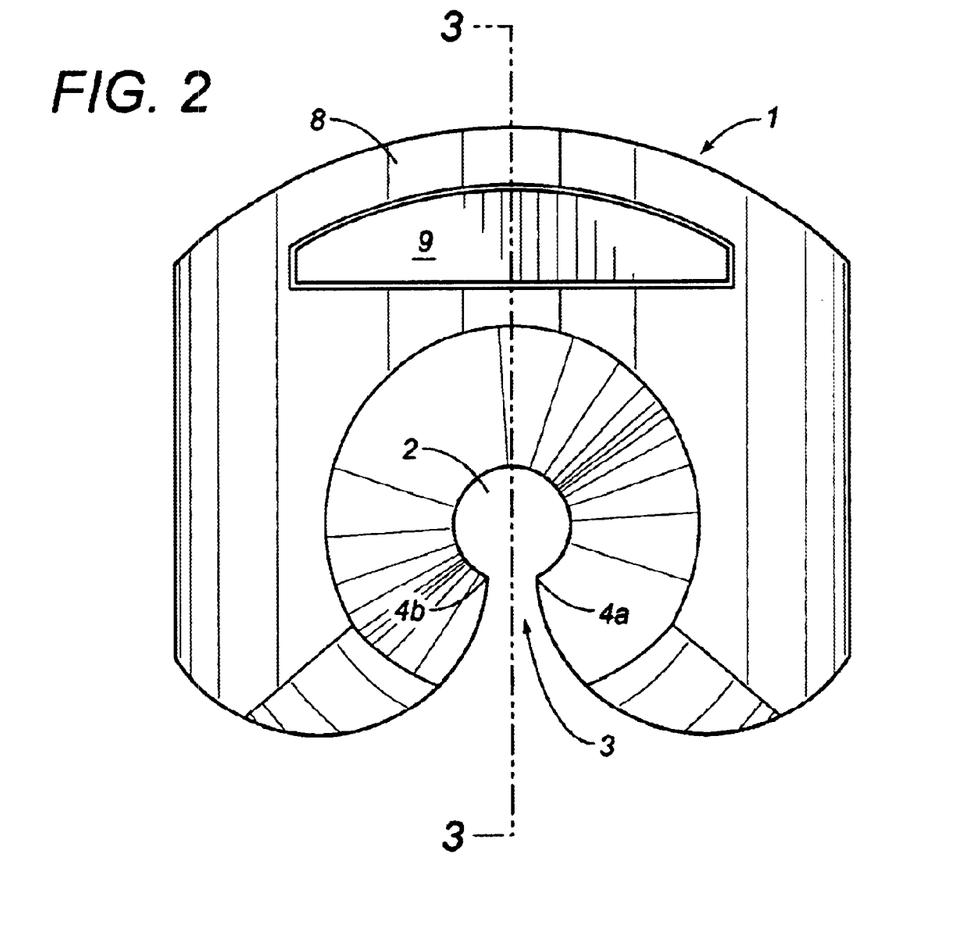
FIG. 2 is a front view of the end of the portion of the support of the identifying device provided with the constrictive housing.
Figure 3:
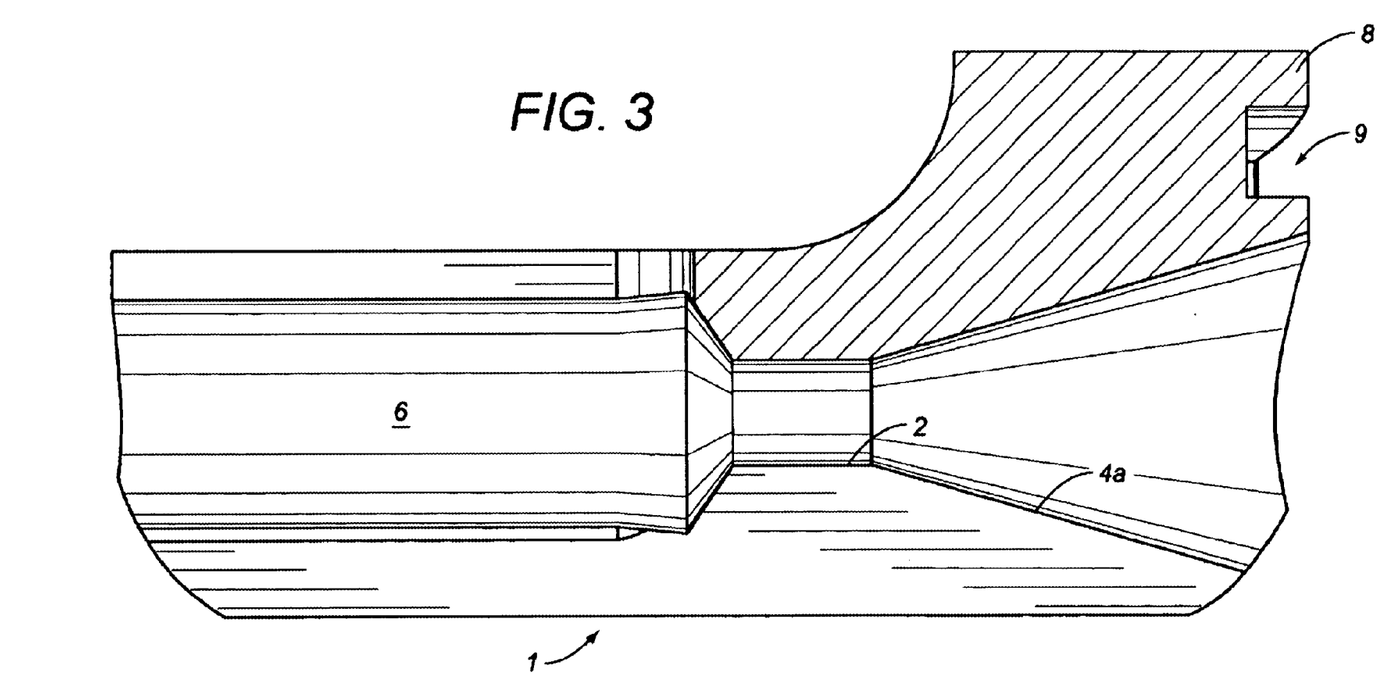
FIG. 3 is an axial section view of the support the identifying device, taken along the line 3—3 of FIG. 2.
Figure 4:
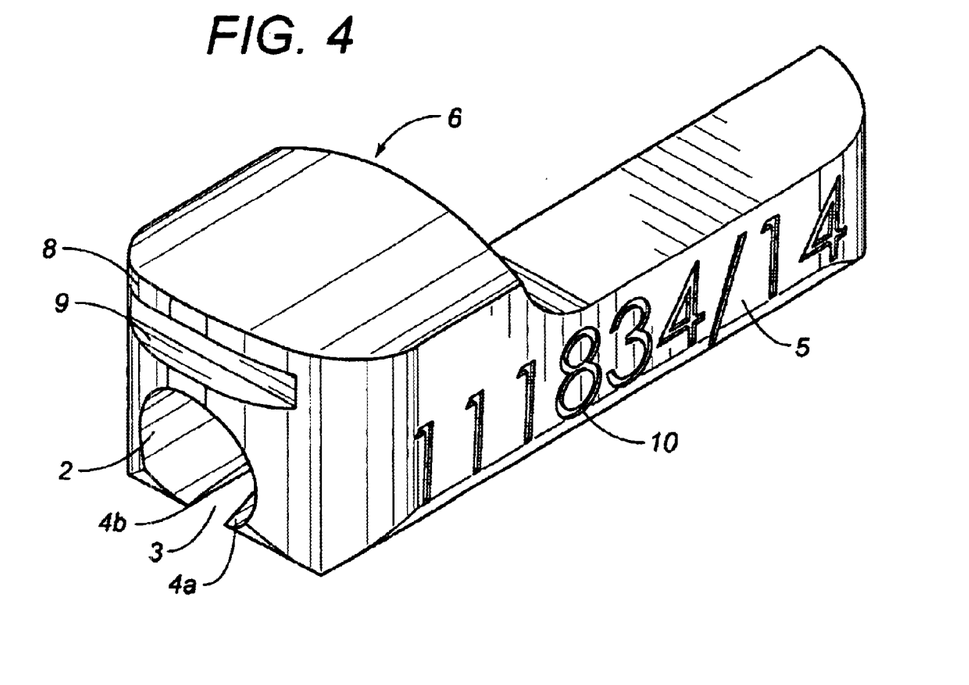
FIG. 4 is a perspective view of the support of the identifying device, taken from the side equipped with the identification engraving.
Figure 5:
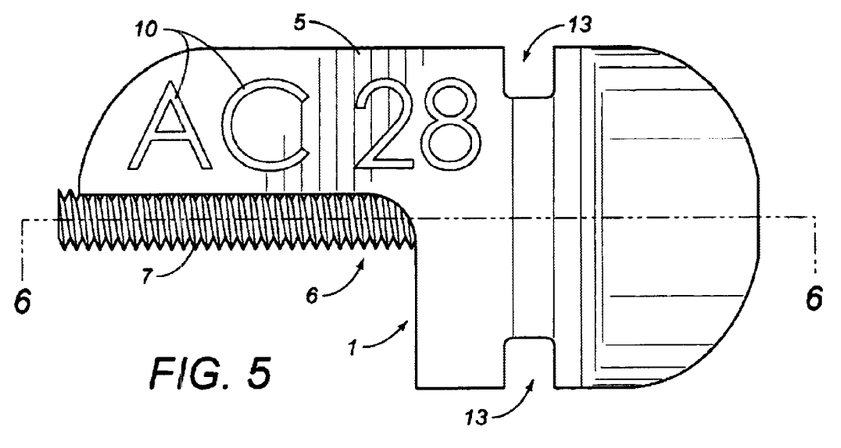
FIG. 5 is a plan view of another embodiment form of the identifying device according to the invention.
Figure 7:
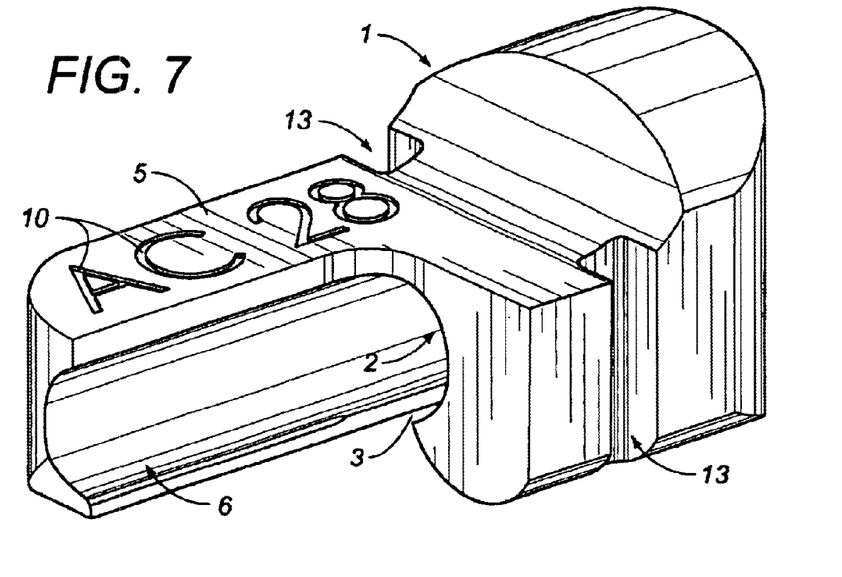
FIG. 7 is a perspective view of the support of the identifying device shown in FIGS. 5 and 6.
Figure 8:
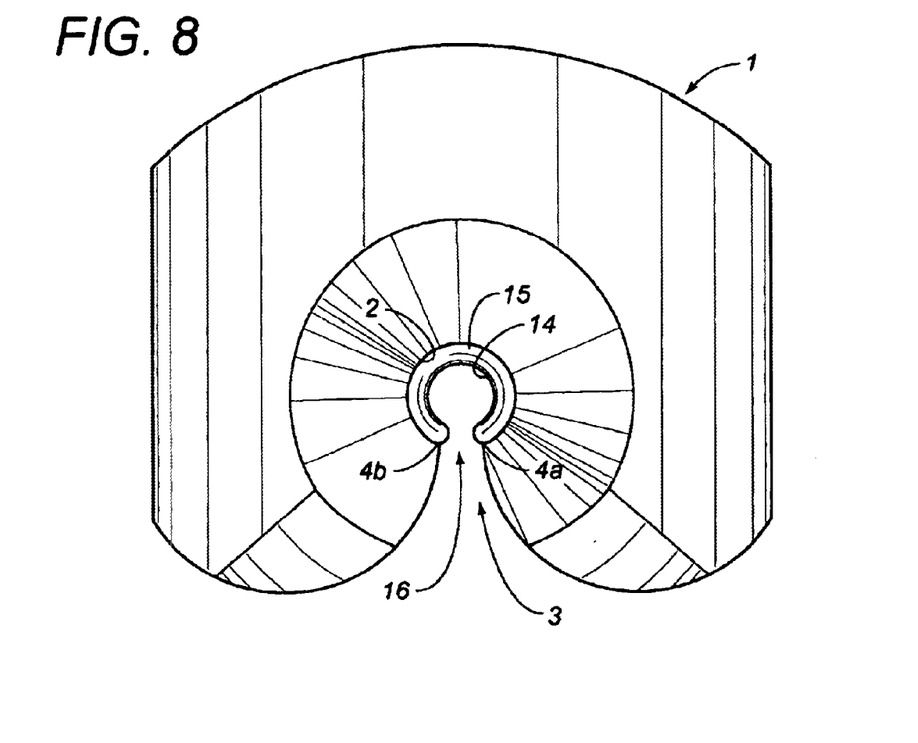
FIG. 8 is a front view of one of the ends of this support.
Figure 9:
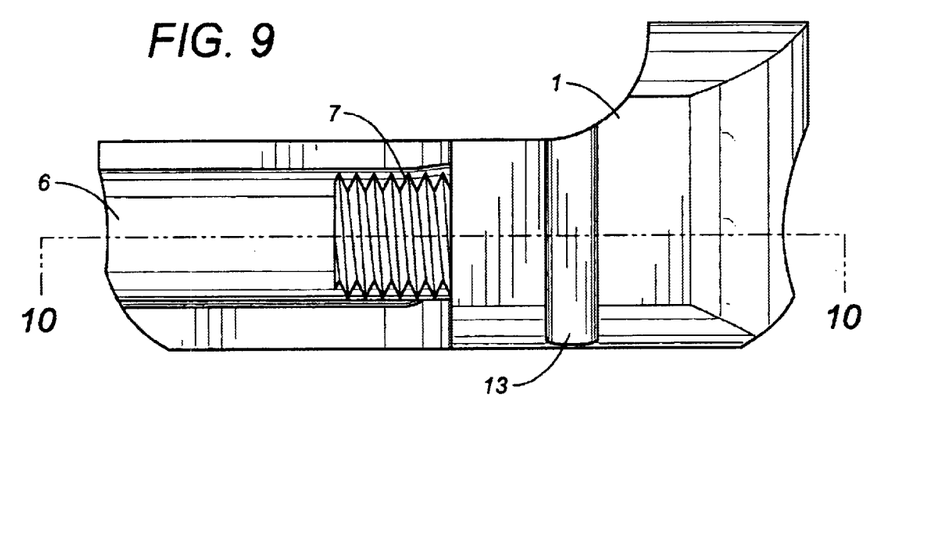
FIG. 9 is a side view showing the matching of an identical support and of a screw having different characteristics from the one shown in FIGS. 5 and 6.

On the side (FIG. 4) or above (FIG. 7), the body has a surface 5, preferably planar and smooth, on which is engraved or otherwise applied, an identification mark 10, for example, made of a lot number that can be easily read. Depending on its placement, this surface can occupy a length corresponding approximately to the length of the body 1 or a length less than that.

When an implant 7 has been positioned in a support 1 that has been individualized by an identification mark 10, it forms with the support an assembly or identifying device whose integrity will not be destroyed when the implant is used by the surgeon.

In a manner of interest, the identifying support consists of an open recess 6 extending longitudinally, over a length approximately equal to the half-length of the body 1. This recess 6 is arranged in the extension of the housing 2 which opens into the recess. This recess makes it possible to easily grasp the implant 7 held in the body 1, with surgical forceps, in order to free it from its support. It also allows, in addition, a good exposure of the implant to the source of sterilization.

The implants and their support matched in this way can be held by pressure into the housings that have the plates used for sterilization and presentation in the surgical unit.

They stay positioned at their positions during their transport by the action of pressure that the supports exert on the walls of their housings under the action of elasticity of material out of which the supports are made.

Figure 11:
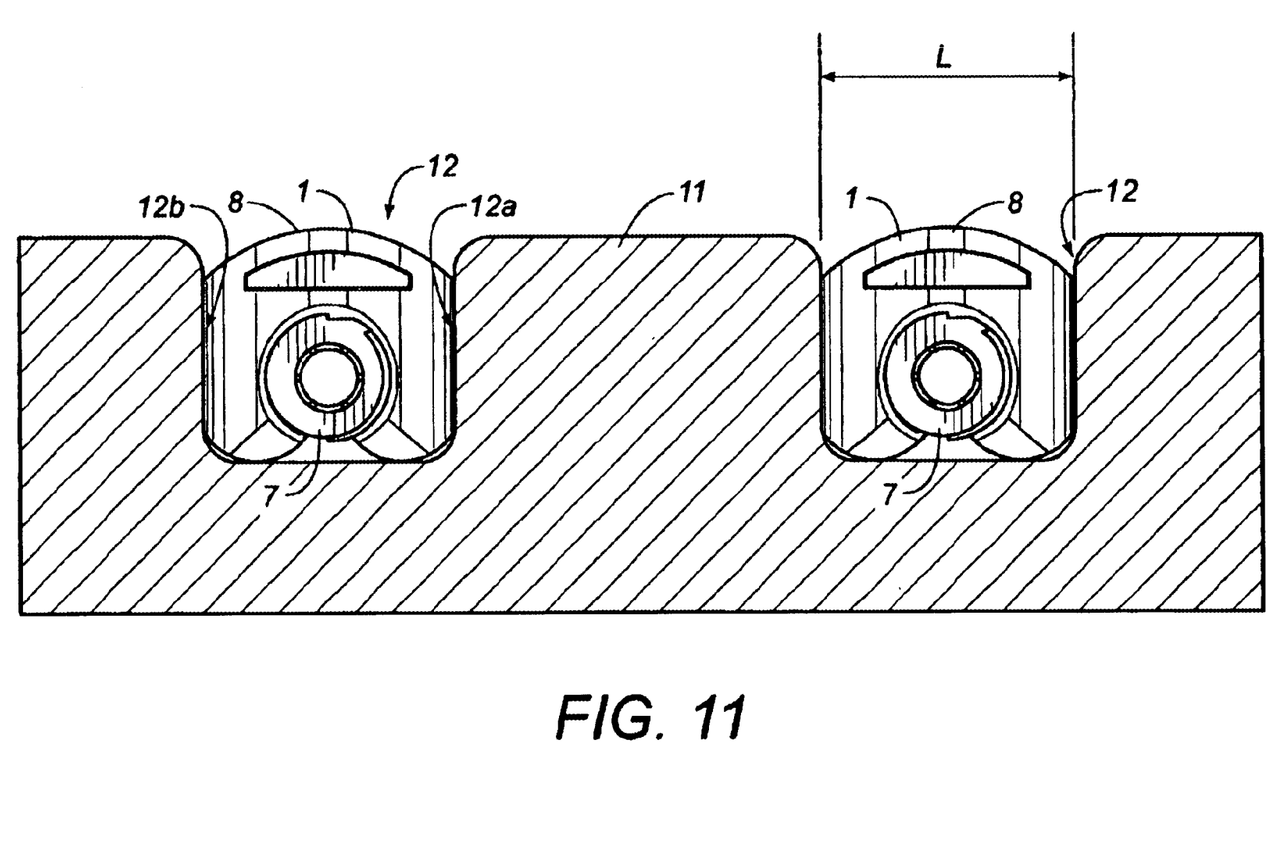
FIG. 11 is a transverse section view of a plate in the longitudinal grooves of which coupled assemblies of identifying support/implant according to the invention are positioned.

Shown in FIG. 11 is a plate 11 consisting of two longitudinal grooves 12 in which two coupled assemblies of matched identifying supports 1/screws 7 are positioned and held, for example, for their use in a surgical unit. The grooves 12 of the plate 11 have a width L very slightly less than that of the identifying devices, in a manner so that these devices can be held by a slight pressure between the walls 12a of the grooves and then are held in position in them due to the elasticity of the elastomer out of which the body 1 is made.

According to another characteristic arrangement, the body 1 of the identifying support has, on the outside, a mechanism intended to make it easier to grasp the identifying device using a surgical procedure instrument (surgical tweezers, for example).

According to the embodiment mode shown in FIGS. 1 to 4, the body 1 consists of a grasping tongue 8 which results, for example, from providing a transverse slit 9 in the free end of the part of the body 1 that bounds the housing 2.

In considering, as indicated above, that the assemblies of the matched identifying support 1/implant 7, are brought in the surgical unit in the plates in which they are positioned in a specified manner by being pinched, the tongue 8 makes it possible to grasp the assembly including the implant desired and to disengage its housing using an appropriate surgical instrument such as surgical tweezers.

According to the embodiment mode shown in FIGS. 5 to 8, the grasping mechanisms of the identifying device 1–7 are made up of two parallel grooves 13 that are, symmetrically, in the opposed lateral sides of the part of the body 1 in which the housing 2 is arranged, these grooves being arranged on each side of the slit 3 opening in the housing. When putting the leading edges of the grasping forceps into the grooves 13, it is easy to disengage the device from the plate and then to remove the implant 7 from the support 1, for example, using another appropriate sterile instrument.

According to another characteristic arrangement of the invention, the housing 2 consists, preferably in its median part, of a narrow section 14 bounded by a smooth circular lip 15. This smooth, compressible lip has a slit 16 that is open into the slit 3 of the body 1. The smooth, slotted lip or collar 15 bounds an axial passage having a diameter that is clearly less than the diameter of the remaining portion of the housing 2.

Figure 6:
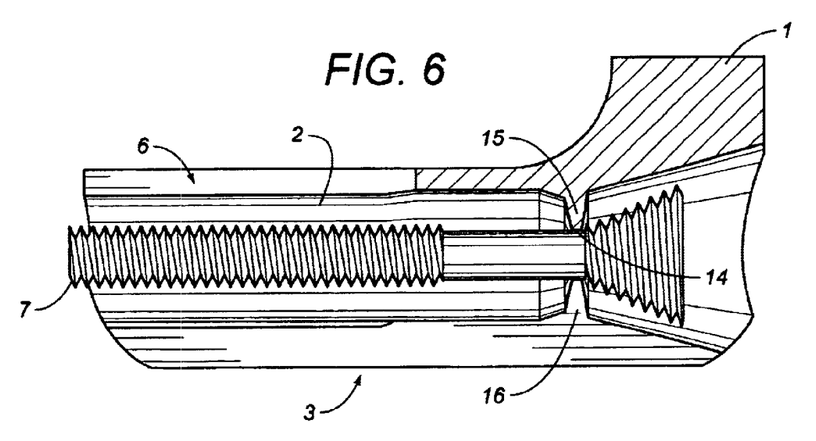
FIG. 6 is a longitudinal section view along the line 6—6 of FIG. 5.
Figure 10:
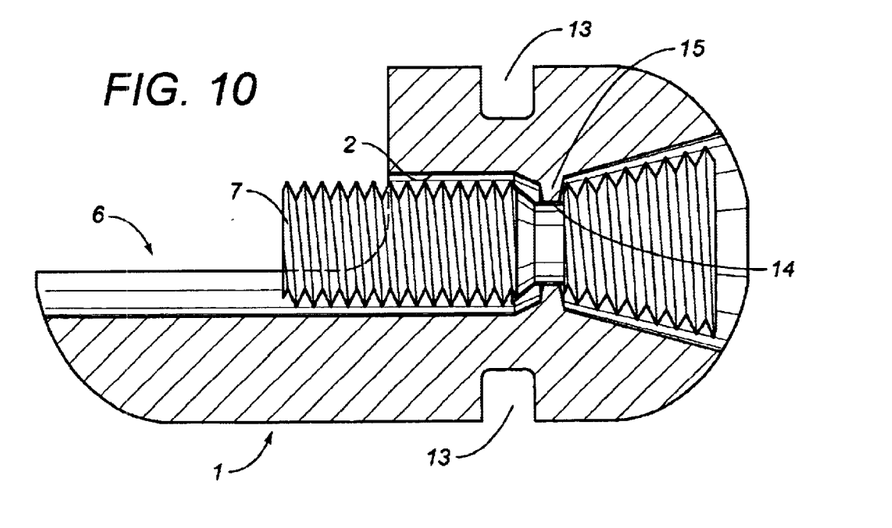
FIG. 10 is a longitudinal section view along line 10—10 of FIG. 9.

Using this arrangement, screws having different diameters or other small implants can be matched to the identical identifying supports, as shown, for example, in FIGS. 6 and 10, which prevents the manufacture and storage of several different sizes of identifying supports 1.

What is claimed is:

1. An identifying device for handling and identification of small implants used for the coaptation of bone fragments and for osteosynthesis comprising:

a small-sized implant; and an identifying support matched to said small-sized implant, said identifying support comprising:

a body made at least partially of an elastically deformable material, said body having a retentive housing, said retentive housing having a form fitted to said small-sized implant, said small-sized implant being at least partially housed in said retentive housing, said body having a slit opening into said retentive housing; and a designation means formed on said identifying support, said designation means for identifying said identifying support, said retentive housing having a constrictive narrow section bounded by a smooth circular lip, said retentive housing holding said small-sized implant by a tightening action exerted upon said retentive housing.

2. The identifying device of claim 1, said smooth circular lip having a slot, said slot being in open communication with said slit of said body.

3. The identifying device of claim 1, said retentive housing extending over only a portion of a length of said body, said body having a recess opening to an outside of said body and extending from a side of said retentive housing opening to said recess opening.

4. The identifying device of claim 1, said identifying support having a grasping mechanism formed on an outside thereof.

5. The identifying device of claim 4, said grasping mechanism comprising two parallel grooves symmetrically contained in opposed lateral sides of said body.

6. The identifying device of claim 1, said body having a planar surface on an exterior thereof, said planar surface having said designation means contained thereon, said designation means being an identification mark.

7. The identifying device of claim 1, further comprising:

a plate having grooves formed thereon, said grooves each having a width slightly less than a width of said identifying support, said identifying support being held in said grooves, said elastically deformable material being an elastomer, said elastomer having an elasticity suitable for holding said identifying support in position.

* * * * *